United States Patent [19]

Errigo

[11] Patent Number: 5,683,718
[45] Date of Patent: Nov. 4, 1997

[54] ENTERIC COATED TABLET WITH RAISED IDENTIFICATION CHARACTER AND METHOD OF MANUFACTURE

[75] Inventor: Joseph A. Errigo, Farmingdale, N.Y.

[73] Assignee: Time-Cap Labs, Inc., Farmingdale, N.Y.

[21] Appl. No.: 416,312

[22] Filed: Apr. 4, 1995

[51] Int. Cl.$^6$ ............... A61K 9/20; A61K 9/28; A61K 9/30; A61K 9/44
[52] U.S. Cl. ............ 424/464; 424/467; 424/474; 424/475
[58] Field of Search ............... 424/490, 464, 424/467

[56] References Cited

U.S. PATENT DOCUMENTS

| | | | |
|---|---|---|---|
| D. 269,713 | 7/1983 | Tovey | D28/2 |
| D. 290,412 | 6/1987 | Downs. | |
| 2,865,810 | 10/1958 | Sanders, Jr. | 167/82 |
| 3,159,544 | 12/1964 | Heffernan | 167/82 |
| 3,173,839 | 3/1965 | Nicholson | 167/82 |
| 4,017,647 | 4/1977 | Ohno et al. | 427/3 |
| 4,465,660 | 8/1984 | David et al. | 424/15 |
| 4,556,552 | 12/1985 | Porter et al.. | |
| 4,629,620 | 12/1986 | Lindahl et al. | 424/15 |
| 4,661,367 | 4/1987 | Forse et al.. | |
| 4,713,248 | 12/1987 | Kjornaes et al.. | |
| 4,716,041 | 12/1987 | Kjornaes et al.. | |
| 4,720,378 | 1/1988 | Forse et al. | 424/6 |
| 5,002,772 | 3/1991 | Curatolo et al.. | |
| 5,002,775 | 3/1991 | Toya et al. | 424/467 |
| 5,256,440 | 10/1993 | Appel et al.. | |
| 5,279,832 | 1/1994 | Greissinger et al.. | |
| 5,391,378 | 2/1995 | Sanderson. | |

Primary Examiner—Thurman K. Page
Assistant Examiner—Sharon Howard
Attorney, Agent, or Firm—Gary M. Nath; Nath & Associates

[57] ABSTRACT

A mechanical configuration for a tablet, and a method for manufacturing the same, which allows an enteric coating to be applied to an embossed bio-compatible tablet, for identification purposes. The enteric coating remains uniform over the entire tablet allowing for release of the drug as designed.

10 Claims, 3 Drawing Sheets

SPHERICAL

SHALLOW

STANDARD

DEEP

FLAT FACE

CAPSULE

FLAT EDGE BEVEL EDGE

OVAL

MODIFIED BALL

SPHERICAL    SHALLOW    STANDARD    DEEP

FLAT FACE    CAPSULE    FLAT EDGE BEVEL EDGE    OVAL    MODIFIED BALL

ENTERIC COATED TABLET WITH RAISED IDENTIFICATION CHARACTER AND METHOD OF MANUFACTURE

BACKGROUND OF THE INVENTION

1. Field of the Invention

The present invention pertains to a mechanical configuration for a tablet, and a method for manufacturing the same, which allows an enteric coating to be applied to an embossed bio-compatible tablet, for identification purposes. The enteric coating remains uniform over the entire tablet allowing for release of the drug as designed.

2. Description of the Prior Art

Certain film coatings are applied to pharmaceutical products in order to modify the release pattern of a drug. One form of coating is used to prevent the release of drugs in, or protect drugs from the effects of, the gastric environment. Such a coating is commonly called an enteric coating.

By definition, enteric coatings are those which remain intact in the stomach, but will dissolve and release the contents of the dosage form once they arrive at the small intestine. Their purpose is to delay the release of drugs which are inactivated by the stomach contents, (e.g., pancreatin, erythromycin) or may cause nausea or bleeding by irritating the gastric mucosa (e.g., aspirin, steroids). In addition, they can be used to give a simple repeat-action effect where unprotected drug coated over the enteric coat is released in the stomach, while the remainder, being protected by the coating, is released further down the gastrointestinal tract.

The action of enteric coatings results from a difference in composition of the respective gastric and intestinal environment in regard to pH and enzymatic properties. Although there have been repeated attempts to produce coatings which are subject to intestinal enzyme breakdown, this approach is not popular since enzymatic decomposition of the film is rather slow. Modern enteric coatings are those which remain undissociated in the low pH environment of the stomach, but readily ionize when the pH rises to about 4 or 5. The most effective enteric polymers are cellulostic phalates having a pH of 3 to 5.5.

The marking of tablets and capsules by drug manufacturers is required by State and federal regulations, as well as being useful to the manufacturers in internal production and quality control concerns. Various methods are used to imprint information on the tablet concerning manufacturer, contents, and quality codes, but enteric coated tablets have not been compatible with all identification methods.

Printed information, applied in the form of one or more colors, can be placed directly on the surface of the tablet. However, printing is a relatively difficult, slow and costly procedure, and requires the use of specialized machinery, and in some cases the imprinting process and/or ink used creates a breach of the enteric coated characteristics of the film.

The use of color coding is another alternative. Color helps the manufacturer to control the quality of the product during its preparation, as well as serving as a means of identification to the user. Also, the use of colors in solid dosage form makes it possible to establish the identity of an unknown compressed tablet in situations arising from poisoning.

The most common method of adding color to a tablet formulation is to dissolve the dye in the binding solution prior to the granulating process. Another approach is to adsorb the dye on starch or calcium sulfate from its aqueous solution; the resultant powder is dried and blended with the other ingredients.

Frequently during drying, colors in wet granulations migrate, resulting in an uneven distribution of the color in the granulation. After compression the tablets will have a mottled appearance due to the uneven distribution of the color. Migration of colors may be reduced by drying the granulation slowly at low temperatures and stirring the granulation while it is drying. Prevention of mottling can be helped also by the use of lubricants and other additives which have been colored similarly to the granulation prior to their use. The problem of mottling becomes more pronounced as the concentration of the colorants increases. Color mottling is an undesirable characteristic common to many commercial tablets.

All colorants used in pharmaceuticals must be approved and certified. Colorants have been subjected to rigid toxicity standards and approved colorants in the U.S. include the following: FD&C Red No. 3, FD&C Red No. 40, FD&C Yellow No. 5, FD&C Green No. 3, a limited number of D&C colorants, and the iron oxides. Each country has its own list of approved colorants and formulators must consider this in designing products for the international market. Thus, there are limited choices available to color tablets and the lack of international standardization can increase production costs.

Another method of marking tablets is by the use of intagliations. Two significant problems which may occur result from the internal stress that develops within a film placed over the intagliations as it dries. The first occurs when this stress exceeds the tensile strength of the film, causing it to crack. The second is manifested as "bridging" and occurs when a component of the internal stress is able to overcome the localized forces of attachment of the film to the tablet in the region of the monogram. The film no longer follows the contour of the indented monogram and draws away to bridge the crevices.

Some examples of the prior art identification methods are:

Appel et al., U.S. Pat. No. 5,256,440, is a process for preparing and film coating a dosage form. An intagliated dosage form core is produced by inscribing one or more areas on the surface of the dosage form core prior to coating. An aqueous dispersion of a polymeric coating is then applied to the intagliated dosage form core. When placed in an environment of use, the film coating within the circumscribed region of the dosage from surface is reproducibly expelled, leaving a coated core tablet with a predefined aperture in the coating which exposes a discrete portion of the core surface to the environment of use.

Forse et al., U.S. Pat. No. 4,661,367, is for colored intagliated articles, for example colored intagliated pharmaceutical tablets, on which the intagliations are highlighted. The articles are colored intagliated articles bearing a layer consisting essentially of a defined optically anisotropic substance, for example magnesium carbonate.

Using the prior art methods for tablet manufacture an enteric coating applied over angles and elevations is thinner than that applied over surfaces without sever topology. Furthermore, enteric coatings pool in crevices or intagliations, and the angular joining of two planes fills with excess coating, creating pockets. Such deficiencies prevent uniform drug release patterns thus making embossing a tablet with an enteric coating previously impractical. Accordingly, only coloring and printing have been available as effective identification methods to mark enteric coatings. These methods, however, increase cost and production time. The present invention remedies these deficiencies.

SUMMARY OF THE INVENTION

A preferred embodiment of this invention comprises a solid tablet containing a drug for administration via the digestive tract, a raised character on said solid tablet, wherein the form of said raised character is a spherical segment, and an enteric coating, wherein said coating is uniformly applied over said tablet and said raised character.

Another preferred embodiment comprises a raised character spherical segment bounded by a top plane and a bottom plane, said top plane comprising the top of said raised character, said bottom plane comprising the surface of said tablet.

Another preferred embodiment comprises a solid tablet containing a drug for administration via the digestive tract, said tablet having a top and bottom, a plurality of raised characters on said solid tablet top and bottom, wherein the form of said raised characters is a spherical segment, an enteric coating, wherein said coating is applied to essentially a uniform thickness over said tablet and said raised characters.

Alternate embodiments have tablets that are cylindrical, oval, square and triangular in shape, or in caplet form.

Another preferred embodiment of this invention is a method of fabricating a tablet, comprising the steps of forming a tablet of a drug for administration via the digestive tract, embossing at least one side of said tablet with a character, wherein the form of said character is a spherical segment, and coating the tablet and character with an enteric coating of essentially uniform thickness.

Another preferred method comprises the steps of placing tableting material in a die cavity, placing a lower punch into a die from the bottom and an upper punch from above, and at least one of said lower and upper punches having a head configured to emboss said tablet with a character, wherein the form of said character is a spherical segment, applying pressure to the punches, ejecting the tablet from the die, and coating the tablet and embossing to an essentially uniform thickness with an enteric coating.

DETAILED DESCRIPTION OF THE PREFERRED EMBODIMENTS

Other objects, features and advantages of the present invention will become apparent to those skilled in the art from the following detailed description and attached drawings. For simplicity and clarity, only one preferred embodiment of the present invention is illustrated, but it is understood that it is not to be construed as limiting the invention thereto, but rather it should be viewed as a representative embodiment of the broader inventive concept.

The basic mechanical unit in all tablet-compression equipment includes a lower punch which fits into a die from the bottom and an upper punch, having a head of the same shape and dimensions, which enters the die cavity from the top after the tableting material fills the die cavity. The tablet is formed by pressure applied on the punches and is subsequently ejected from the die. The weight of the tablet is determined by the volume of the material which fills the die cavity. Therefore, the ability of the tablet blend to flow freely into the die is important in insuring an uniform fill, as well as the continuous movement of same from the source of supply or feed hopper. If the tablet blend does not possess cohesive properties, the tablet after compression will crumble and fall apart on handling. As the punches must move freely within the die and the tablet must be readily ejected from the punch faces, the material must have a degree of lubrication to minimize friction and to allow for the removal of the compressed tablets.

There are three general methods of tablet preparation: (1) the wet-granulation method; (2) the dry-granulation method; and (3) direct compression. The method of preparation and the added ingredients are selected in order to give the tablet formulation the desirable physical characteristics allowing the rapid compression of tablets. After compression the tablets must have a number of additional attributes such as appearance, hardness, disintegration ability, appropriate dissolution characteristics, and uniformity which are also influenced both by the method of preparation and by the added materials present in the formulation. The tablet assumes the size and shape of the punches and die used.

Figure 1:
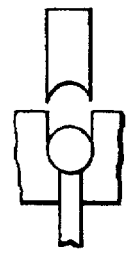
FIG. 1 depicts a variety of dies and punches which can be used to form the tablet of the present invention.
Figure 1:
Figure 1:
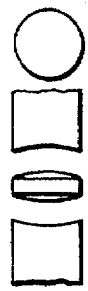
Figure 1:
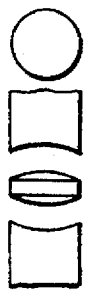
Figure 1:
Figure 1:
Figure 1:
Figure 1:
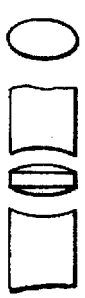
Figure 1:

While round tablets are preferred, ovals, caplets, square, triangular, or other irregular shapes may be used. Likewise, the curvature of the faces of the punches determines the curvature of the tablets. FIG. 1 depicts some common die shapes used to manufacture tablets.

By employing a spherical surface with a raised identification symbol, an enteric coating is able to be applied which does not obliterate the symbol by blending it into the surface of the tablet. It also enables the coating to be applied by conventional spray drying techniques, well known in the art, which use a rotary side vented coating pan or other suitable tablet coating and drying devices without the chipping of the edges or corners from the tablet or the coating varying in its thickness which will result in the premature release of the drug when contacting the stomach.

The following description relates to one preferred embodiment but should be viewed as merely a representative description of the invention as a whole and not its complete embodiment.

Figure 2:
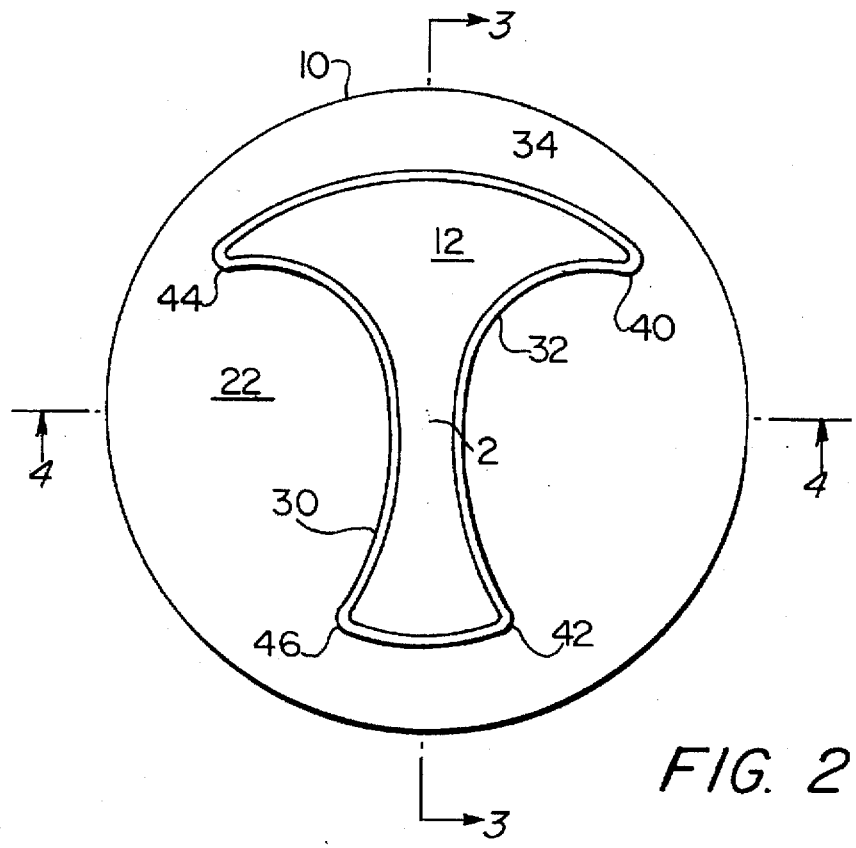
FIG. 2 is a top plan view of the tablet of the present invention.

Referring to FIG. 2 of the drawings, there is depicted medicinal tablet 10 having embossed character 12. In order to prevent any weakening of the enteric coating at the edges or build up of coating, embossed character 12 has no sharp edges or corners. All transitions from one plane to another are gradual and carefully designed to allow an enteric coating of uniform thickness. Sides 34 and 36 are concave to center 2 of tablet 10, and sides 30, 32 are convex to center 2. The junction of sides 34 and 36 with side 30 and 32 at corners 40, 42, 44, 46 are all concave to center 2.

The curvature of sides 30, 32, 34 and 36 is critical to enable effective coating of the tablet with an enteric coating substance. A preferred range of curvature for sides 30 and 32 is between about 0.025 and 0.4 radians with a most preferred range of about 0.075 to 0.229 radians. The preferred range of values for the curvature of sides 34 and 36 is between about 0.05 and 0.3 radians, with a most preferred range of about 0.105 to 0.255 radians. A preferred range of values for the curvature of corners 40 and 44 is from about 0.005 to 0.15 radians with a most preferred range of from about 0.009 to 0.013 radians. A preferred range for the curvature of corners 46 and 42 is from about 0.005 to 0.15 radians with a most preferred range of about 0.007 to 0.010 radians.

Figure 3:
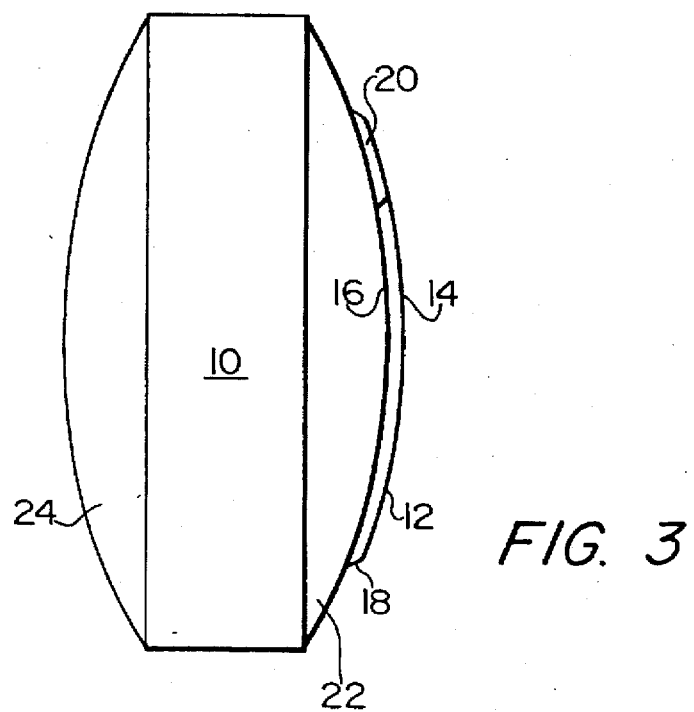
FIG. 3 is a cross sectional view of FIG. 2 along the lines 3—3.

FIG. 3 depicts a cross section of tablet 10 and embossed character 12. The cross section of embossed character 12 is a spherical segment bounded by two planes 14, 16. The length of the edge of plane 14 is less than that of the edge of plane 16, which causes sides 18, 20 to slope beyond the vertical and form obtuse angles with surface 22 of tablet 10. In the depicted preferred embodiment both side 22 and 24 are curved, however only side 22 with embossing 12 is required to be curved.

Figure 4:
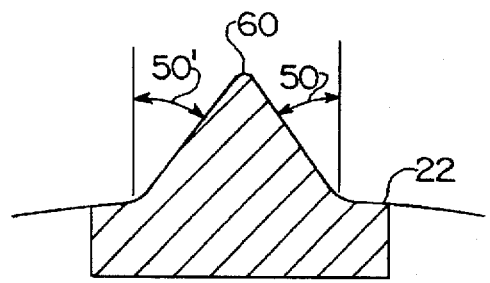
FIG. 4 is a cross sectional view of FIG. 2 along the lines of 4—4.

FIG. 4 depicts a cross sectional view of tablet 10 along the lines 4—4 of FIG. 2. Angles 50, 50', as measured from the normal, at which embossing 12 joins surface 22 of tablet 10 are critical. Angles less than 90 degrees and preferably from about 25 degrees to about 75 degrees are useable with preferred angles from about 35 to 60 degrees being highly effective. For symmetrical characters angles 50 and 50' must be about equal but dissimilar angles can be used to form alternate embodiments.

Peak 60 of embossed character 12 is the highest point of plane 14 above surface 22. If peak 60 is excessively high this will result in chipping of the enteric coating during the coating and drying process. A preferred range of heights for peak 60 is from about 0.015 to 0.05 centimeters with a most preferred range from about 0.02 to 0.025 centimeters in height. Also, to prevent chipping peak 60 must present a rounded surface. The preferred range of curvature for peak 60 is from about 0.0010 to 0.0020 radians with a most preferred range of about 0.0013 to 0.0017 radians.

Figure 5:
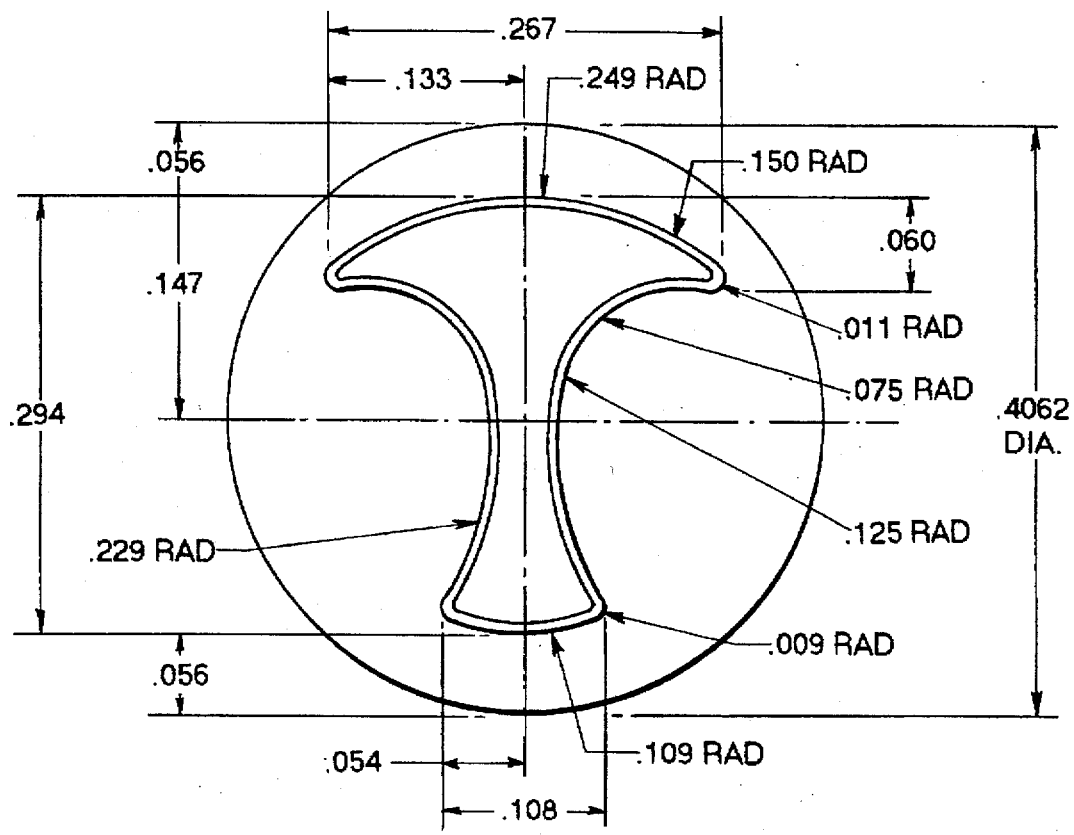
FIG. 5 is a top plan view of a preferred embodiment of the present invention.

FIG. 5 depicts a preferred embodiment of the present invention incorporating the most preferred ranges of curvature and height.

Enteric coatings on solid pharmaceutical dosage forms, such as, tablets, pills, granules, caplets and the like has been carried out by a method comprising coating the dosage forms with various enteric-coating materials dissolved in an organic solvent with the addition, if necessary, of plasticizers and coloring agents.

Enteric coatings may also be applied by coating the tablet with an aqueous solution of a polymeric substance having carboxyl groups in the water-soluble salt form and bringing the thus coated dosage forms into contact with an inorganic acid to convert the polymeric substance into the acid form which is insoluble in water.

Another method of applying enteric coatings is to use an aqueous suspension of a pH sensitive enteric coating polymer such as polyvinylacetate phthalate or cellulose acetate phthalate or a mixture thereof in combination with a plasticizing agent such as triethyl citrate.

Any conventional coating machine such as pan coaters, rotary drum coaters, of fluidizing coaters may be used to apply the coating to the embossed tablet. The thickness of the coating film should be determined by the kinds of polymeric substances employed, the types and quantities of materials added, the ratio of the mixtures of the polymeric substances and the other materials, the pH values of the internal juices, and the disintegration time in the intestinal juice selected.

The invention being thus described, it will be obviously that the same may be varied in many ways. Such variations are not to be regarded as a departure form the spirit and scope of the invention and all such modifications are intended to be included within the scope of the following claims.

What is claimed is:

1. A tablet, comprising:

a solid tablet containing a drug for administration via the digestive tract;

a raised character on said solid tablet, wherein said raised character is a spherical segment having an angle less than 90 degrees where said raised character joins the surface of said solid tablet; and an enteric coating, wherein said enteric coating is uniformly applied over said solid tablet and said raised character.

2. The tablet of claim 1 wherein said raised character spherical segment is bounded by a top plane and a bottom plane, said top plane comprising the top of said raised character, said bottom plane comprising the surface of said solid tablet.

3. The tablet of claim 1 wherein said solid tablet is cylindrical in shape.

4. The tablet of claim 1 wherein said solid tablet is oval in shape.

5. The tablet of claim 1 wherein said solid tablet is in caplet form.

6. The tablet of claim wherein said solid tablet is square in form.

7. The tablet of claim 1, wherein said solid tablet is triangular shaped.

8. A method of fabricating a tablet, comprising the steps of:

forming a tablet of a drug for administration via the digestive tract;

embossing at least one side of said tablet with a raised character, wherein said raised character is a spherical segment having an angle less than 90 degrees where said raised character joins the surface of said tablet; and coating the tablet and raised character with an enteric coating of essentially uniform depth.

9. The method of claim 8 further comprising:

wherein said method of forming a tablet comprises placing tableting material in a die cavity;

placing a lower punch into a die from the bottom and an upper punch from above, and at least one of said lower and upper punches having a head configured to emboss said tablet with a character, wherein said character is a spherical segment;

applying pressure to the punches;

ejecting the tablet from the die; and coating the tablet and embossing to an essentially uniform thickness with an enteric coating.

10. A tablet, comprising:

a solid tablet containing a drug for administration via the digestive tract, said solid tablet having a top and bottom;

a plurality of raised characters on said solid tablet top and bottom, wherein said raised characters are a spherical segment having an angle less than 90 degrees where said raised characters join the top and bottom of said solid tablet; and;

an enteric coating, wherein said enteric coating is applied to essentially a uniform thickness over said solid tablet and said raised characters.

* * * * *